US006846800B1

(12) United States Patent
Johannsson et al.

(10) Patent No.: US 6,846,800 B1
(45) Date of Patent: *Jan. 25, 2005

(54) METHOD FOR TREATING A PATIENT HAVING METABOLIC SYNDROME

(75) Inventors: Gudmundur Johannsson, Göteborg (SE); Per Mårin, Göteborg (SE); Lars Lönn, Göteborg (SE); Malin Ottosson, Göteborg (SE); Kaj Stenlöf, Göteborg (SE); Per Björntorp, Göteborg (SE); Lars Sjöström, Göteborg (SE); Bengt-Åke Bengtsson, Göteborg (SE)

(73) Assignee: Pharmacia AB, Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/050,366

(22) Filed: Mar. 31, 1998

Related U.S. Application Data

(63) Continuation of application No. 08/857,245, filed on May 16, 1997, now abandoned.
(60) Provisional application No. 60/017,822, filed on May 17, 1996.

(51) Int. Cl.$^7$ .......................... A61K 38/00; A61K 38/28
(52) U.S. Cl. .................. 514/2; 514/3; 514/12; 530/303; 530/324
(58) Field of Search ....................... 514/12, 3; 530/303, 530/324

(56) References Cited

U.S. PATENT DOCUMENTS

| 5,268,277 A | | 12/1993 | Grandi et al. ............... 435/69.4 |
| 5,426,096 A | * | 6/1995 | Sonksen et al. .............. 514/12 |

OTHER PUBLICATIONS

Johansson et al., "Growth Hormone–Deficient Adults are Insulin–Resistant" Metabolism, vol. 44, No. 9, pp 1126–1129, 1995.*
Holly etal., J. Endocr., vol. 118, pp. 353–364, 1988.*
Salomon et al., N. Engl. J. Med., vol. 321, No. 26, pp. 1797–1803, Dec. 28, 1989.*
Per Björntorp, "Visceral Obesity: A 'Civilization Syndrome'," Obesity Research, vol. 1, No. 3, May 1993, pp. 206–221.
Gerald M. Reaven, "Role of Insulin Resistance in Human Disease," Diabetes, vol. 37, Dec. 1988, pp. 1595–1607.
B–Å Bengtsson, "The Consequences of Growth Hormone Deficiency in Adults," Acta Endrocrinological, 128 Suppl. 2: 2–5, 1993, pp. 2–5.
Gerald M. Reaven, "Pathophysiology of Insulin Resistance in Human Disease," Physiological Review, vol. 75, No. 3, Jul. 1995, pp. 473–486.

Salomon, F., et al., "The Effects of Treatment with Recombinant Human Growth Hormone on Body Composition and Metabolism in Adults with Growth Hormone Deficiency," The New England Journal of Medicine, vol. 321, No. 26, Dec. 28, 1989, pp. 1797–1803.
Johansson, Jan–Ove, et al., "Growth Hormone—Deficient Adults are Insulin–Resistant," Metabolism, vol. 44, No. 9, Sep. 1995, pp. 1126–1129.
Rosén, Thord, et al., "Cardiovascular Risk Factors in Adult Patients with Growth Hormone Deficiency," Acta Endocrinologica, 1993, vol. 129 pp. 195–200.
Johansson, Jan–Ove, et al., "High Fibrinogen and Plasminogen Activator Inhibitor Activty in Growth Hormone–Deficient Adults," Arteriosclerosis and Thrombosis, vol. 14, No. 3, Mar. 1994, pp. 434–437.
Markussis, Viron, et al., "Detection of Premature Atherosclerosis by High–Resolution Ultrasonography in Symptom–Free Hypopituitary Adults," The Lancet, vol. 340, Nov. 14, 1992, pp. 1188–1192.
Mårin, P., et al., "Endocrine–Metabolic Pattern and Adipose Tissue Distribution," Hom Res, 39 (suppl 3), 1993, pp. 81–85.
Rosén, Thord, and Bengtsson, Bengt–Åke, "Premature Mortality Due to Cardiovascular Disease in Hypopituitarism," The Lancet, vol. 336, Aug. 4, 1990, pp. 285–288.
Mårin, P., et al., "Cortisol Secretion in Relation to Body Fat Distribution in Obese Premenopausal Women," Metabolism, vol. 41, No. 8, Aug. 1992, pp. 882–886.
Mårin, P., et al., "Low Concentrations of Insulin–Like Growth Factor–I in Abdominal Obesity," International Journal of Obesity, vol. 17, 1993, pp. 83–89.
Mårin, P., et al., "Androgen Treatment of Abdominally Obese Men," Obesity Research, vol. 1, No. 4, Jul. 1993, pp. 245–251.
Veldhuis, J.D., et al., "Differential Impact of Age, Sex Steroid Homones, and Obesity on Basal Versus Pulsatile Growth Hormone Secretion in Men as Assessed in an Ultrasensitive Chemiluminescence Assay," Journal of Clinical Endocrinology and Metabolism, vol. 80, No. 11, 1995, pp. 3209–3222.
Hartman, M.L., et al., "A Low Dose Euglycemic Infusion of Recombinant Human Insulin–Like Growth Factor I Rapidly Suppresses Fasting–Enhanced Pulsatile Growth Hormone Secretion in Humans," J. Clin. Invest., vol. 91, Jun. 1993, pp. 2453–2462.

(List continued on next page.)

Primary Examiner—Christopher S. F. Low
Assistant Examiner—Abdel A. Mohamed
(74) Attorney, Agent, or Firm—Dinsmore & Shohl LLP

(57) ABSTRACT

Methods for treating a patient for insulin resistance to decrease the insulin resistance in a patient having Metabolic Syndrome comprising Primary Insulin Resistance and abdominal/visceral obesity comprise administering to the patient growth hormone or a functional derivative thereof in an amount effective for decreasing insulin resistance of the patient.

4 Claims, 3 Drawing Sheets

OTHER PUBLICATIONS

De Boer, H., et al., "Clinical Aspects of Growth Hormone Deficiency in Adults," *Endocrine Reviews*, vol. 16, No. 1, 1995, pp. 63–86.

Landin–Wilhelmsen, K., et al., "Serum Insulin–Like Growth Factor I in a Random Population Sample of Men and Women: Relation to Age, Sex, Smoking Habits, Coffee Consumption and Physical Activity, Blood Pressure and Concentrations of Plasma Lipids, Fibrinogen, Parathyroid Hormone and Osteocalcin," *Clinical Endocrinology*, vol. 41, 1994, pp. 351–357.

Kvist, H., et al., "Apiose Tissue Volume Determination in Males by Computed Tomography and $^{40}$K," *International Journal of Obesity*, vol. 12, 1988, pp. 249–266.

Chowdhury, B., et al., "A Multicompartment Body Composition Technique Based on Computerized Tomography," *International Journal of Obesity*, vol. 18, 1994, pp. 219–234.

*Lipoprotein Analysis A Practical Approach*, C.A. Converse and E.R. Skinner, eds., Oxford University Press, New York, New York, 1992, pp. ix–xv.

Dole, V.P., and Meinertz, H., "Microdetermination of Long–Chain Fatty Acids in Plasma and Tissues," *The Journal of Biological Chemistry*, vol. 235, No. 9, Sep. 1960, pp. 2595–2599.

Friberger, P., et al., "Methods for Determination of Plasmin, Antiplasmin and Plasminogen by Means of Substrate S–2251," *Haemostasis*, vol. 7, 1978, pp. 138–145.

Larsson, Bo, et al., "Obesity, Adipose Tissue Distribution and Health in Men—The Study of Men Born in 1913," *Appetite*, vol. 13, 1989, pp. 37–44.

Marcus, R., et al., "Effects of Short Term Administration of Recombinant Human Growth Hormone to Elderly People," *Journal of Clinical Endocrinology and Metabolism*, vol. 70, No. 2, pp. 519–527.

Rudman, D., et al., "Effects of Human Growth Hormone in Men Over 60 Years Old," *The New England Journal of Medicine*, vol. 323, No. 1, Jul. 5, 1990, pp. 1–6.

Bengtsson, B–Å, et al., "Treatment of Adults with Growth Hormone (GH) Deficiency with Recombinant Human GH," *Journal of Clinical Endocrinology and Metabolism*, vol. 76, No. 2, 1993, pp. 309–317.

Rosenbaum, M., et al., "Effects of Systemic Growth Hormone (GH) Administration on Regional Adipose Tissue Distribution and Metabolism in GH–Deficient Children," *Journal of Clinical Endocrinology and Metabolism*, vol. 69, No. 6, 1989 pp. 1274–1281.

Bolli, G.B., and Gerich, J.E., "The 'Dawn Phenomen'—A Common Occurrence in Both Non–Insulin–Dependent and Insulin–Dependent Diabetes Mellitus," *The New England Journal of Medicine*, vol. 310, No. 2, Mar. 22, 1984, pp. 746–750.

Fowelin, J., et al., "Combined Effect of Growth Hormone and Cortisol on Late Posthypoglycemic Insulin Resistance in Humans," *Diabetes*, vol. 38, Nov. 1989, pp. 1357–1364.

Fowelin, J., et al., "Effects of Treatment with Recombinant Human Growth Hormone on Insulin Sensitivity and Glucose Metabolism in Adults with Growth Hormone Deficiency," *Metabolism*, vol. 42, No. 11, Nov. 1993, pp. 1443–1447.

DeFronzo, R.A., et al., "Effects of Insulin on Peripheral and Splanchnic Glucose Metabolism in Noninsulin–Dependent (Type II) Diabetes Mellitus," *J. Clin. Invest.*, vol. 76, Jul. 1985, pp. 149–155.

Lund, S., et al., "Comparative Effects of IGF–I and Insulin on the Glucose Transporter System in Rat Muscle," 1994 the American Physiological Society, pp. E461–E466.

Ayling, C.M., et al., "Human Growth Hormone Treatment of Hypophysectomized Rats Increases the Proportion of Type–1 Fibres in Skeletal Muscle," *Journal of Endocrinology*, vol. 123, 1989, pp. 429–435.

Rudling, M., et al., "Importance of Growth Hormone for the Induction of Hepatic Low Density Lipoprotein Receptors," *Proc. Natl. Acad. Sci. USA*, vol. 89, Aug. 1992, pp. 6983–6987.

Bo Angelin and Mats Rudling, "Growth Hormone and Hepatic Lipoprotein in Metabolism," *Current Opinion in Lipidology*, vol. 5, 1994, pp. 160–165.

Elam, M.B., et al., "In Vitro Growth Hormone Treatment Stimulates Secretion of Very Low Density Lipoprotein by the Isolated Perfused Rat Liver," *Endocrinology*, vol. 131, No. 6, pp. 2717–2722.

Richelsen, B., et al., "Growth Hormone Treatment of Obese Women for 5 wk: Effect on Body Composition and Adipose Tissue LPL Activity," The American Physiology Society, 1994, pp. E211–E216.

Reaven, G.M., et al., "Hypertension and Associated Metabolic Abnormalities—The Role of Insulin Resistance and the Sympathoadrenal System," *The New England Journal of Medicine*, vol. 334, No. 6, Feb. 8, 1996, pp. 374–381.

Copeland, K.C., and Sreekumaaran Nair, K., "Recombinant Human Insulin–Like Growth Factor–I Increases Forearm Blood Flow," *Journal of Clinical Endocrinology*, vol. 79, No. 1, 1994, pp. 230–232.

Landin, K., et al., "Abdominal Obesity is Associated with an Impaired Fibrinolytic Activity and Elevated Plasminogen Activator Inhibitor–1," *Metabolism*, vol. 39, No. 10, Oct. 1990, pp. 1044–1048.

Hamsten, A., et al., "Plasminogen Activator Inhibitor in Plasma: Risk Factor for Recurrent Myocardial Infarction," *The Lancet*, Jul. 4, 1987, pp. 3–9.

Wilhelmsen, L., et al., "Fibrinogen as a Risk Factor for Stroke and Myocardial Infarction," *The New England Journal of Medicine*, vol. 311, No. 8, Aug. 23, 1984, pp. 501–505.

Mårin, P., et al., "The Effects of Testosterone Treatment on Body Composition and Metabolism in Middle–Aged Obese Men," *International Journal of Obesity*, Vo. 16, 1992, pp. 991–997.

Liu, L., et al., "Chronic Sex Steroid Exposure Increases Mean Plasma Growth Hormone Concentration and Pulse Amplitude in Men with Isolated Hypogonadotropic Hypogonadism," *Journal of Clinical Endocrinology and Metabolism*, vol. 64, No. 4, 1987, pp. 651–656.

Yang, S., et al., "Additive Effects of Growth Hormone and Testosterone on Lipolysis in Adipocytes of Hypophysectomized Rats," *Journal of Endocrinology*, vol. 147, 1995, pp. 147–152.

Jorgenssen et al, Horm. Res. 42, 1994, 235–241.

Bengtsson et al, Acta. Paediatr. Suppl. 382, 1992, 62–65.

Hew et al, Endocrin. Metabol. 3, 1996, 55–60.

Johansson et al, J. of Clin. Endocrin. 82 (8), 1997.

* cited by examiner

A

B

METHOD FOR TREATING A PATIENT HAVING METABOLIC SYNDROME

CROSS-REFERENCE TO RELATED APPLICATIONS

This is a continuation of our U.S. application Ser. No. 08/857,245 filed May 16, 1997, entitled Use Growth Hormone and now abandoned; which in turn claims priority from U.S. Provisional Application Ser. No. 60/017,822 filed May 17, 1996.

The present invention relates to the use of growth hormone, preferably human growth hormone or analogues thereof for the manufacturing of a medicament for treatment of individuals with Metabolic Syndrome (also labeled Syndrome X). They include individuals with abdominal/visceral obesity and its metabolic and circulatory consequences including insulin resistance, lipoprotein aberrations and hypertension. The medicament is also used to increase insulin sensitivity and for treatment and prevention of non-insulin dependent diabetes mellitus.

BACKGROUND ART

Strikng similarities exhibits between The Metabolic Syndrome[1, 2] (also labeled Syndrome X or Primary Insulin Resistance Syndrome) and untreated GH deficiency in adults[3]. The most central findings in both these syndromes are abdominal/visceral obesity and insulin resistance[1,4-6]. Other features common to both conditions are high triglyceride and low high-density lipoprotein cholesterol concentrations, an increased prevalence of hypertension, elevated levels of plasma fibrinogen and plasminogen activator inhibitor-1 activity, premature atherosclerosis and increased mortality from cardiovascular diseases[1, 4,7-11].

The Metabolic Syndrome is associated with multiple endocrine abnormalities. They include increased cortisol secretion, blunted secretion of gonadotrophins and sex steroids and abnormalities in the GH/insulin-like growth factor-I (IGF-I) axis [12-14]. With increased adiposity GH secretion is blunted with decreased mass of GH secreted per burst but without any major impact on GH secretory burst frequency [15]. The serum IGF-I concentration is principally GH dependent and influences GH secretion though a negative feed-back system [16]. The serum levels of IGF-I are inversely related to the percentage body fat [15]. In addition, we have previously shown that the low serum IGF-I concentration in obesity is predominantly related to the amount of visceral adipose tissue and not to the amount of subcutaneous fat mass [13]. These findings, together with other endocrine disturbances in central obesity, suggest that the low GH secretion which is observed is secondary to a central disturbance of the neuroendocrine regulation, including the GH/IGF-I axis.

The abdominal/visceral obesity and insulin resistance observed in The Metabolic Syndrome constitute the base for hypertension, dyslipoproteinemia and non-insulin dependent diabetes mellitus. [1]

Replacement therapy with recombinant human GH (rhGH) has demonstrated favorable effects on most of the features of GH deficiency in adults [17]. Whether rhGH treatment can improve the metabolic abnormalities observed in abdominal/visceral obesity has never been investigated.

SUMMARY OF INVENTION

In the present study a randomized, double-blind, placebo-controlled design was used to evaluate the effects of rhGH administration in patients with abdominal/visceral obesity.

In the present study thirty men, 48 to 66 years of age with abdominal/visceral obesity were treated with recombinant human GH (rhGH) in a 9-month randomized, double-blind, placebo-controlled trial. Body fat was assessed from total body potassium and abdominal subcutaneous and visceral adipose tissue was measured using computed tomography. Glucose disposal rate (GDR) was measured during euglycemic, hyperinsulinemic glucose damp.

In response to the rhGH treatment, total body fat, abdominal subcutaneous and visceral adipose tissue decreased. The GDR (glucose disposal rate) increased in the rhGH-treated group as compared with the placebo-treated one. The mean serum concentrations of total cholesterol and triglyceride decreased while blood glucose and serum insulin concentrations were unaffected by the rhGH treatment. Furthermore, diastolic blood pressure decreased and systolic blood pressure was unchanged in response to rhGH treatment.

The present study has demonstrated that GH can favorably affect some of the multiple perturbations associated with The Metabolic Syndrome. This includes a reduction in abdominal/visceral obesity an improved insulin sensitivity and favorable effects on lipoprotein metabolism and diastolic blood pressure. Thus, the prevention and treatment of non-dependent diabetes mellitus may be possible.

The findings must be regarded as unexpected and surprising and of utmost interest giving a possibility to treat and prevent diseases associated with increased cardiovascular morbidity and mortality.

The present invention thus relates to the use of growth hormone or analogues thereof as claimed in the claims on file.

By analog is meant a substance having the same biological activity as described here and having at least 65% homology with natural occurring growth hormone.

BEST AND VARIOUS MODES FOR CARRYING OUT INVENTION

EXAMPLE

Subjects and Methods

Patients

Figure 1:
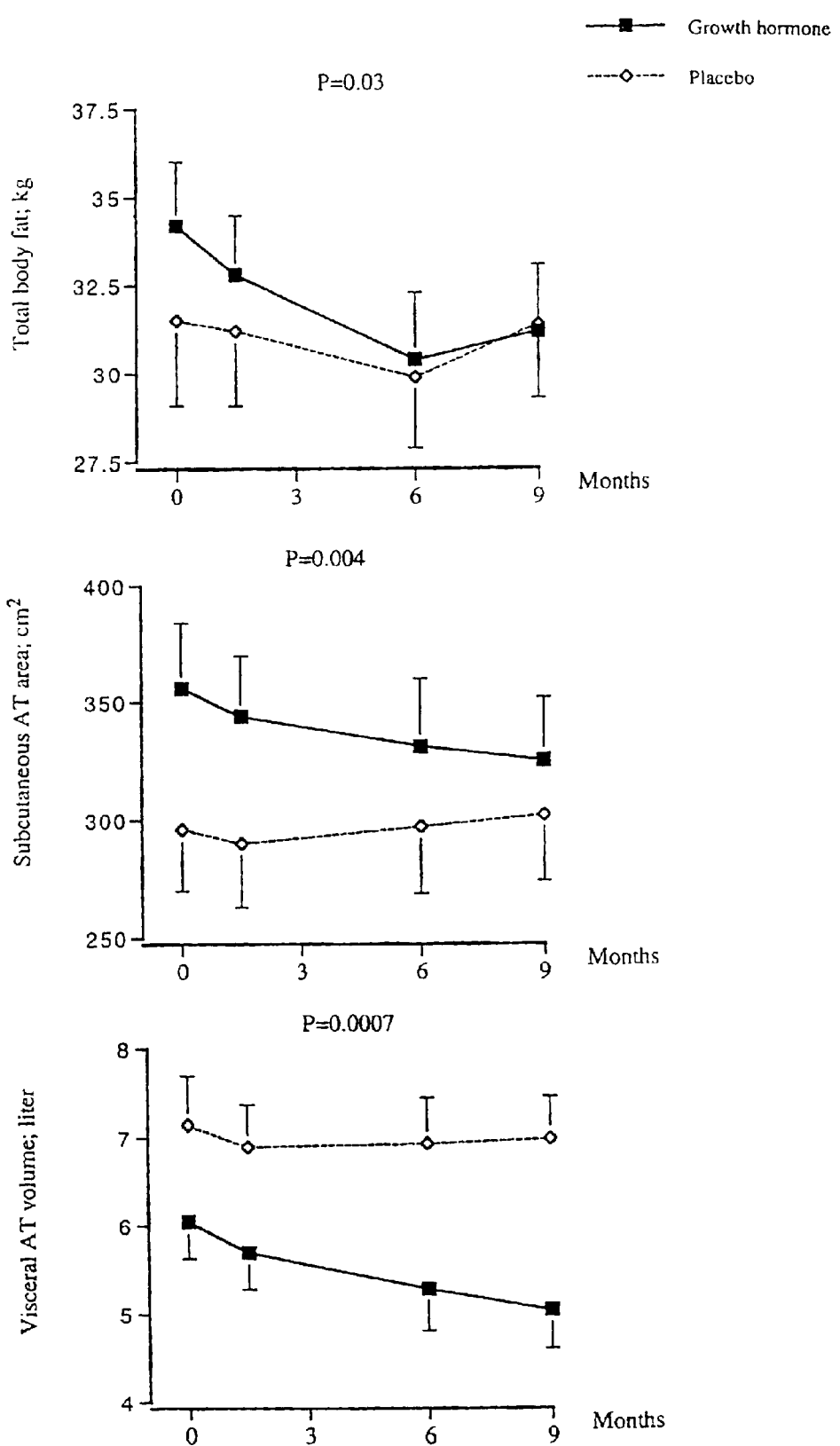
FIG. 1 illustrates mean total body fat calculated from total body potassium, abdominal subcutaneous adipose tissue (AT) area at the level of L4–L5 and volume of visceral AT assessed with computerized tomography during 9 months of treatment with rhGH or placebo in 30 men with abdominal/visceral obesity. The horizontal bars indicate the SE for the mean values shown and p-values denotes the differences between the two groups by two-way ANOVA for repeated measurements.

Thirty men (48 to 66 years of age) were studied (Table 1). They were recruited by advertisement in a local newspaper. The criteria for inclusion in the study were age approximately 50 to 65 years with a body mass index between 25 and 35 kg/m$^2$, an IGF-I less that 160 µg/L (low normal) [18] and a waist hip ratio of more that 0.95. The criteria for exclusion were overt diabetes mellitus, previous cardiovascular event or heart disease.

In the rhGH treated group, two patients were receiving treatment for hypertension with both atenolol (100 mg per day) and nifedipin (40 mg per day) and one patient had slight asthma, treated with salmeterol and terbutalin inhalations. In the placebo treated group, one patient had a slight depressive disorder and was receiving paroxetin (10 mg per day). These medications were kept stable during the study period.

Study Design

This study was a 9 month randomized, double-blind, placebo-controlled trial of the administration of rhGH. Informed consent was obtained from each patient before the study. The study was approved by the Ethics Committee at the University of Göteborg and by the Swedish Medical Products Agency, Uppsala, Sweden.

Treatment

The daily rhGH dose was 9.5 µg/kg (0.20 IU/kg body weight/week), administrated subcutaneously before bedtime. The dose was reduced by half in the event of side-effects. The average dose reduction during the 9-month study was 0.17 mg per day (range −1.7 to 0). The placebo vials contained the same vehicle as the rhGH vials and both preparations were visually indistinguishable. Compliance assessed by counting the returned empty vials and expressing that number as a percentage of vials needed for the treatment period was 87.3% (range, 32–100).

Study Protocol

The patients were studied as out-patients before and after 6 weeks, 6 and 9 months is of treatment Physical and laboratory examinations were performed at all visits. The euglycemic hyperinsulinemic clamp, adipose issue needle aspiration and measurement of blood pressure and heart rate were performed at baseline, 6 weeks and after 9 months of treatment Body weight was measured in the morning to the nearest 0.1 kg wearing indoor clothing, and body height was measured barefoot to the nearest 0.01 m. The body mass index was calculated as body weight in kilograms divided by height in meters squared. Waist circumference was measured in the standing position with a flexible plastic tape midway between the lower rib margin and the iliac crest, and the hip girth at the widest part of the hip. Systolic and diastolic blood pressure were measured after 5 minutes of supine rest using the sphygmanometric cuff method. This measurement was repeated after one minute and the mean value was used.

Total-body potassium was measured by counting the emission of 1.46 MeV gamma-radiation from the naturally occurring $^{40}$K isotope in a high-sensitive 3π whole body counter with a coefficient of variation (CV) of 2.2%. Fat-free mass (FFM) was estimated by assuming a potassium content of 64.7 mmol/kg FFM [19] and body fat (BF) was calculated as body weight-FFM. A five-scan computed tomography technique was used (Philips Tomoscan 350) to measure abdominal adipose tissue. The five levels were derived from two scanograms and included one scan at the level of the mid-thigh with the lower edge of symphysis as a reference point. The other four levels were the lower edge of symphysis, L4–5 lumbar disc, L3–4 lumbar disc and a scan at the level of liver and spleen. The tissue areas and anatomic boundaries were determined as described previously [20].

Total volume of visceral adipose tissue was determined from the five scan model. Sagittal diameter and abdominal subcutaneous and visceral adipose tissue areas were determined at the level of L4–5.

A euglycemic, hyperinsulinaemic glucose clamp was performed after an overnight fast as previously described [14]. In brief, insulin was infused together with glucose into a venous catheter with the tip at the level of the axillary vein at appropriate rates to obtain submaximal insulin concentrations. Blood glucose concentrations were monitored every 10 min. and glucose infusion rate was adjusted to fasting levels. Glucose disappearance rate (GDR) was measured for 20 minutes in steady-state conditions, which was reached after 100 min. The insulin concentrations during steady state were 214±10 µIU/mL before treatment, 226±12 µIU/mL at 6 weeks and 213:±11 µIU/mL at 9 months. During the clamp, in steady-state conditions, a subcutaneous abdominal adipose tissue biopsy was obtained by needle aspiration for the determination of lipoprotein lipase (LPL) activity. The needle aspiration was performed under local anesthesia, 0.1 m lateral to the umbilicus. The biopsies were immediately frozen in liquid nitrogen and stored at −80-C. until assay.

Analytic Methods

Total LPL activity in adipose tissue was determined after homogenization of the tissue in the detergent-containing buffer as described previously [21]. Bovine skim milk was used as a standard to correct for interassay variation. The amount of triglycerides (TG) in the tissue was measured after extraction [22] and weighed after evaporation of solvents. Activity was expressed in milliunits (1 mU=1 mmol FFA released per min.) per gram adipose tissue and per gram TG. Control experiments showed that the assay was linear with the amount of sample and incubation time, over the range used. The within-assay CV was 43%.

Blood samples were drawn in the morning after an overnight fast. The serum concentration of insulin-like growth factor-I (IGF-I) was determined by a hydrochloric acid-ethanol extraction radioimmunoassay using authentic IGF-I for labeling (Nichols Institute Diagnostics, San Juan Capistrano, Calif., USA) with within-assay CV of 2.5% and 4.2% at serum concentrations of 125 µg/L and 345 µg/L respectively. The standard deviation score for IGF-I was then calculated from predicted IGF-I values adjusted for age and sex obtained from the normal population [18].

The insulin-like growth factor binding protein-3 (IGFBP-3) concentration in serum was determined by radioimmunoassay (Nichols Institute Diagnostics) with total CV of 6.2% and 5.7% at serum concentrations of 2.05 mg/L and 3.49 mg/L respectively.

Serum cholesterol and triglyceride concentrations were determined with enzymatic methods (Boehringer, Mannheim, Germany). The within-assay CV for total cholesterol and triglyceride determinations was 0.9% and 1.1% respectively.

Fibrinogen was measured according to a syneresis method [23] with a total CV of 4% at 2.5 g/L. Plasminogen activator inhibitor (PAI)-1 activity was measured using a Spectrolyse (pL) PAI kit (Biopool Stabilyte, Umeå, Sweden) with a total CV of 10% at concentrations between 10–40 IU/ml.

Serum insulin was determined by a radioimmunoassay (Phadebas, Pharmacia, Uppsala, Sweden) and blood glucose was measured by the glucose-6-phosphate dehydrogenase method (Kebo Lab, Stockholm, Sweden). Hemoglobin Alc (HbA1c) was determined by high pressure liquid chromatography (Wates, Millipore AB, Sweden) and C-peptide was determined by a radioimmunoassay (Santec, USA). Free fatty acids (FFA) levels were determined using an enzymatic colorimetric method (NEFAC; Wako, Neuss, Germany), while sex hormone binding globulin (SHBG) was measured by an immunoradiometric assay (Farrmos, Diagnostica, Åbo, Finland) and total testosterone by a radioimmunoassay (ICM, Biomedical, Costa Mesa, USA).

Statistical Methods

All descriptive statistical results are presented as the means and standard error of the mean (SEM). Comparisons between the two treatment groups were performed by a two-way analysis of variance (ANOVA) for repeated measurements. Comparisons between baseline values and values at 9 months in the two groups were performed with the Students' t-test for independent groups. Correlations were sought by calculating the Pearson linear correlation coefficient. Pearson's chi square test was used to test the independence of frequency of hypertension and smoking between the rhGH and placebo treated groups. Before statistical analysis, logaritmic transformation of data with skewed distribution was performed. A two-tailed probability value of less than 0.05 was considered significant.

Results

The two groups were matched with regard to age, body height, body weight and waist hip ratio, and did not differ significantly regarding number of subjects with medically treated hypertension (Chi sqr.=1.87; p=0.17) and current smokers (Chi sqr.=1.2; p=0.27) (Table 1). At baseline the two groups did not differ significantly from each other in any of the variables studied.

Body Composition

The patients' mean overall body mass index and fat-free mass did not change while mean total body fat decreased by 9.2±2.4% during rhGH treatment in comparison with placebo treatment (FIG. 1). Waist circumference and sagittal diameter decreased in response to rhGH while no change occurred in the placebo group. Moreover, abdominal subcutaneous and visceral adipose tissue area at the level of L4–5 decreased in response to rhGH by 6.1±3.2% and 18.1±7.6% respectively (FIG. 1 and Table 2). The corresponding values in the placebo group were +2.0±2.8% and −3.2±7.6% respectively. Moreover, the volume of visceral adipose tissue decreased in the rhGH treated group by 17.9±3.5% while no change was observed in the placebo treated group (−0.2±4.2%) (FIG. 1).

Thus, the percentage of visceral adipose tissue of the total adipose tissue at the level of L4–5 decreased by 14.5±3.8% while the percentage of subcutaneous adipose tissue of the total adipose tissue at the level of L4–5 increased by 5.4±1.7% in the rhGH-treated group.

Figure 2:
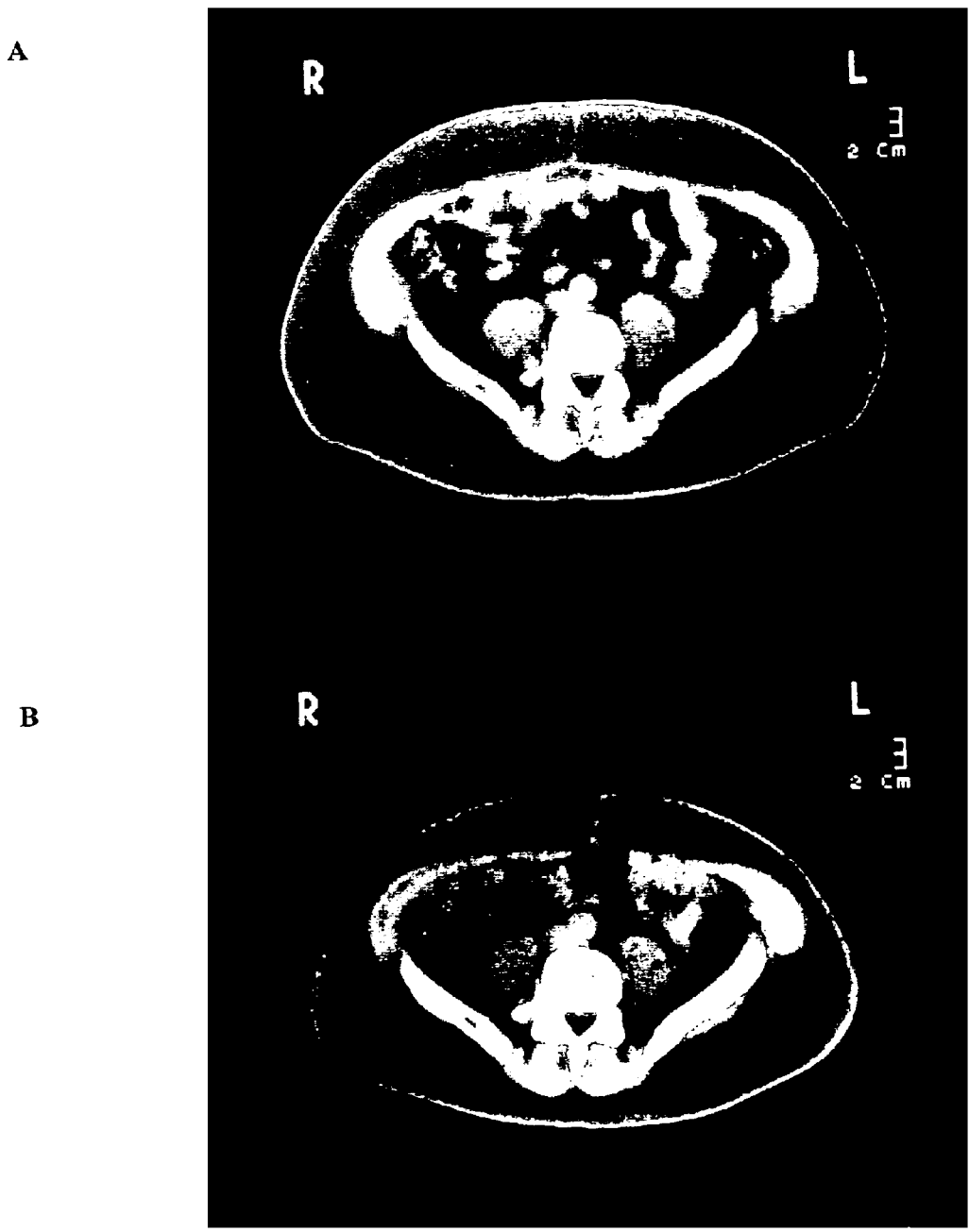
FIG. 2 illustrates abdominal subcutaneous and visceral adipose tissue determined with computed tomography at the level of L4–L5 in one man before (A) and after 9 months of rhGH treatment (B). The scan shows the reduction of both visceral and subcutaneous adipose tissue (shown as dark gray area in the Fig.)

Abdominal subcutaneous and visceral adipose tissue was determined with computed tomography at the level of L4–5 in one man before (A) and after 9 months of rhGH treatment (B). The scan showed a reduction of both visceral and subcutaneous adipose tissue. (FIG. 2)

Glucose Metabolism

Figure 3:
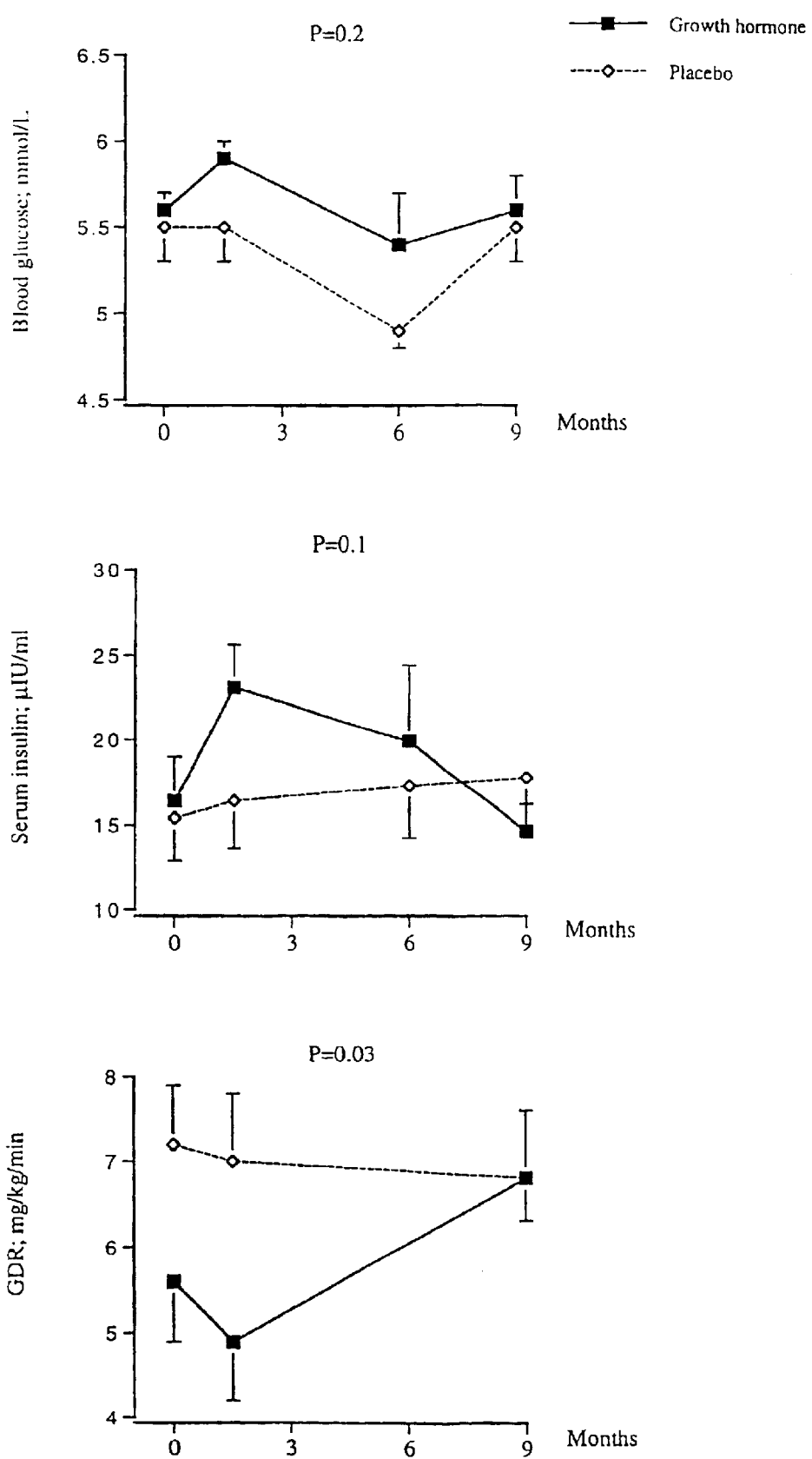
FIG. 3 illustrates mean fasting blood glucose, serum insulin and glucose disappearance rate (GDR) assessed with euglycemic hyperinsulinemic glucose clamp during 9 months of treatment with rhGH or placebo in 30 men with abdominal/visceral obesity. The horizontal bars indicate the SE for the mean values shown and p-values denotes the differences between the two groups by two-way ANOVA for repeated measurements.

No significant effects were elicited by rhGH treatment on blood glucose, serum insulin and HbAlc (Table 3 and FIG. 3). The serum concentration of C-peptide increased in the rhGH treated group due to a transient increase at 6 weeks, but the C-peptide level was similar in the two groups at 9 month.

In the rhGH treated group the GDR showed an initial decrease after 6 weeks of treatment followed by an increment while the placebo-treated group demonstrated a slight reduction over time (FIG. 3). The average increase in GDR in response to 9 months of rhGH was 1.2±0.7 mg/kg/min compared with baseline while in the group receiving placebo a slight decrease by 0.4±0.6 mg/kg/min occurred. This difference between the two groups was still found after correcting the GDR for the amount of fat-free mass.

In the rhGH treated group, an inverse correlation was found between the chance in GDR and change in serum triglyceride concentration (r=−0.58; p<0.05) but no significant correlations were found between the change in GDR and changes in serum IGF-I concentration (r=−0.24), serum insulin concentration (r=−0.27), LPL activity (r=−0.09), diastolic blood pressure (r=−0.30), total body fat (r=0.06) and volume of visceral adipose tissue (r=−0.11).

Total Cholesterol, Triglycerides, LPL Activity, Plasma Fibrinogen and PAI-1 Activity
(Table 3)

The mean total cholesterol concentration decreased from 6.1±0.2 to 5.4±0.3 mmol/L and the triglyceride concentration decreased from 2.09±0.29 to 1.78±0.23 mmol/L in response to rhGH treatment. The corresponding changes in the placebo group were from 5.4±0.3 to 5.5±0.2 mmol/L and from 1.65±0.13 to 2.05±0.26 mmol/L respectively.

The mean total LPL activity in subcutaneous abdominal tissue did not change during rhGH treatment in comparison with placebo treatment. However, between 6 weeks and 9 months, LPL activity tended to increase in the rhGH treated group as compared with the placebo treated group (p=0.06). Similar results were obtained when LPL activity was expressed in mU/g TG.

The plasma concentration of fibrinogen increased in response to rhGH while PAI-I activity was unaffected by rhGH treatment as compared with placebo.

Blood Pressure and Heart Rate

Diastolic blood pressure decreased from 75±2 to 70±2 mmHg in the rhGH treated group. The corresponding values in the placebo group were from 73±2 to 74±2 mmHg (p<0.05). No significant effects on systolic blood pressure or heart rate were observed between the two treatment groups.

Serum IGF-I, IGFBP-3, Testosterone and SHBG (Table 4)

Before treatment, the serum IGF-I concentration was low normal in both treatment groups. A significant increment in serum IGF-I and IGFBP-3 concentrations occurred in the rhGH treated group as compared with placebo treatment. At 6 weeks, the serum IGF-I concentration reached on average 3.30±0.35 SD above the predicted mean in the rhGH treated group while at 9 month the mean serum IGF-I concentration was 1.89±0.48 SD above the predicted mean. Serum concentrations of testosterone and SHBG were not significantly affected by rhGH treatment.

Side-effects

No drop-outs occurred during the study. Side-effects were observed in 8 subjects in the rhGH treated group, and were mainly a result of fluid retention. Five had peripheral edema, two subjects experienced muscle stiffness and arthralgia, one developed mild carpal tunnel syndrome and one subject experienced increased perspiration. These side-effects appeared during the first 6 weeks of treatment and subsided in four patients in response to a reduction in dose performed within 4 months after start of treatment; in three patients, the side-effects subsided spontaneously. One man from the rhGH treated group with medically treated hypertension was taken off treatment after 8 months when he experienced an intracerebral hemorrhage. Three subjects in the placebo group experienced slight and transient peripheral edema.

Discussion

We have shown that 9 months of rhGH treatment in middle-aged men with abdominal/visceral obesity reduced total body fat and resulted in a specific and marked decrease of both abdominal subcutaneous and visceral adipose tissue.

Insulin sensitivity assessed with euglycemic glucose clamp technique improved and serum concentrations of total cholesterol and triglyceride decreased. Furthermore, diastolic blood pressure decreased.

The men who were studied were moderately obese with a preponderance of abdominal and/or visceral localization of body fat as judged from comparisons with randomly selected men of comparable age from the same city [24]. As a group, they had slight to moderate metabolic changes known to be associated with abdominal/visceral obesity with moderate insulin resistant as judged from the GDR values obtained during the euglycemic glucose clamp, although no one had overt diabetes.

Although, we used a lower daily rhGH dose than previously reported in trials studying healthy adults [25,26], the initial rhGH doses administered were apparently too high as judged by the frequency of side-effects and initial high average serum IGF-I concentrations. After dose reduction the average serum IGF-I concentration where within he normal range indicating that the doses of rhGH during the latter part of the study were more physiological. This might in turn explain the less marked anabolic action of the rhGH treatment demonstrated in tis study in comparison with previous trials in healthy adults [25,26].

The marked effect of GH replacement on body composition in GH-deficient adults has been a consistent observation in many studies [17]. The profound lipolytic effect of GH was also demonstrated in the present study with a preferential reduction in visceral adipose tissue depots [27]. These changes have been associated with a GH-induced reduction in the antilipolytic effects of insulin, which is markedly different in different adipose tissue regions [28].

GH exerts direct insulin-antagonistic effects even after the administration of physiological doses of rhGH. GH has been considered to be the principal factor in the decrease in insulin sensitivity observed in the early morning, the so called "dawn phenomenon" [29] and the insulin resistance following hypoglycemia [30]. Thus, our observation of increased insulin sensitivity during prolonged rhGH treatment is unexpected although not inexplicable. We have previously shown that 6 weeks of rhGH treatment in GH-deficient adults only induced a temporary decrease in insulin sensitivity which after 6 months of treatment was restored to baseline values [31]. The response of GDR to rhGH treatment on in this trial showed a similar initial tendency to induce insulin resistance but after 9 months a marked improvement was found. This improvement could be explained by the decreased visceral adipose tissue mass induced by GH, followed by decreased FFA exposure to the liver counteracting the insulin-antagonistic effects of GH. Alternatively, as the major site of glucose disposal is in the skeletal muscle [32] it has to be considered that the improvement in GDR in response to the more prolonged rhGH treatment might also be an effect of increased glucose transport in the skeletal muscle possibly mediated through the ICF-I receptor [33], increased proportion of insulin-sensitive type I muscle fibers [34] or increased capillarization in the skeletal muscle.

GH has been found to be an important regulator of the hepatic LDL-receptor [35] and the overall lipoprotein metabolism [36]. The reduction in total cholesterol is conceivable an effect of enhanced hepatic LDL receptor activity in response to GH[35]. In healthy adults, short-term rhGH administration has been reported to increase serum triglyceride concentration [25]. In this study, the serum triglyceride concentration also displayed an initial increase in response to rhGH treatment. This could be an effect of both an increased flux of FFA to the liver and a direct stimulatory effect on the esterification of oleic acid into triglyceride and phospholipids in hepatocytes [37] in response to GH which in turn enhances the very low density lipoprotein production from the liver. However, after 9 months of rhGH treatment serum triglyceride concentration had decreased again, probably as an effect of the increased insulin-stimulated glucose uptake which is known to be inversely related with the very low density lipoprotein secretion rate from the liver and serum triglyceride levels [4].

The initial tendency of a decline in LPL activity observed in the present study is in accordance with a previous 2 weeks treatment trials with rhGH [38]. During the more prolonged rhGH treatment, however, LPL activity tended to increase which may, at least in part, explain the decrease in serum triglyceride concentration at 9 months. The changes in GDR and LPL activity showed a similar biphasic pattern in response to GH. It may thus be speculated that the suggested influence of GH on LPL activity is mediated through insulin sensitivity, since insulin is known to be a potent stimulator of LPL.

Nine months of rhGH treatment reduced diastolic blood pressure without affecting systolic blood pressure. This is in line with results from GH-deficient adults where rhGH administration reduced diastolic blood pressure possibly as an effect of reduced peripheral vascular resistance [39]. The mechanisms behind the reduction in peripheral vascular resistance might be indirect through the reduced abdominal obesity and increased insulin sensitivity [40] or more direct through the action of IGF-I on the vascular wall [41].

Abdominal/visceral obesity is associated with increased plasma fibrinogen concentration and PAI-I activity [42,43] which both are established risk factors for myocardial infarction and stroke [44,45]. The slightly increased plasma fibrinogen concentration in response to GH may be mediated through increased serum IGF-I concentration [18]. In GH-deficient adults, 2 years of rhGH treatment tended to decrease plasma fibrinogen levels and diminish PAI-1 activity [46]. This further illustrates the importance of the duration of rhGH treatment on the metabolic effects of GH.

Previous studies have shown that testosterone treatment of middle-aged men with abdominal/visceral obesity induced improved insulin sensitivity, plasma lipid levels, diastolic blood pressure as well as a specific decrease of visceral adipose tissue mass [14,46]. Since testosterone treatment of men with hypogonadotrophic hypogonadism increases GH secretion [47] the similarities between testosterone and rhGH treatment might be explained by increased GH levels or by additive or synergistic effects of GH and testosterone on adipose tissue metabolism [48].

The multiple endocrine alterations associated with abdominal/visceral obesity can either be primary responsible or be the consequence of the obese condition. This is the first trial clearly to demonstrate favorable effects of GH on the multiple perturbations associated with abdominal/visceral obesity. We therefore suggest that a blunted GH secretion could be an important factor in the development of the metabolic and circulatory consequences of abdominal/visceral obesity. The metabolic effects demonstrated in this study are probably of importance for the risk of cardiovascular morbidity and mortality in men with abdominal and central adiposity.

TABLE 1

Clinical characteristics of the cohort of 30 men treated with GH or placebo for 9 months.

| Patient characteristics | GH | Placebo |
|---|---|---|
| Number of men | 16 | 14 |
| Mean age (range); years | 58.3 (48–66) | 57.9 (52–63) |
| Treated hypertension; no. | 2 | 0 |
| Present smokers; no. | 5 | 2 |
| Body height; m | 1.80 ± 0.02* | 1.77 ± 0.02 |
| Body weight; kg | 101.7 ± 2.4 | 96.2 ± 2.6 |
| Waist hip ratio | 1.01 ± 0.01 | 1.03 ± 0.02 |

*Plus-minus values are means ± standard error of the mean.

TABLE 2

Measurements of body mass index (BMI), fat free mass, waist circumference, sagital diameter and abdominal visceral adipose tissue (AT) area at the level of L4-5 in 30 men, during 9 months of rhGH or placebo treatment.

| Variable | Baseline | 6 weeks | 6 months | 9 months | P# |
|---|---|---|---|---|---|
| BMI; kg/m² | | | | | |
| GH | 31.4 ± 0.7 | 31.6 ± 0.7 | 31.3 ± 0.7 | 31.1 ± 0.8 | 0.2 |
| Placebo | 30.5 ± 0.8 | 30.6 ± 0.7 | 30.5 ± 0.8 | 30.7 ± 0.8 | |
| Fat free mass; kg | | | | | |
| GH | 67.5 ± 1.8 | 69.7 ± 1.9 | 71.1 ± 1.8 | 69.5 ± 2.2 | 0.4 |
| Placebo | 64.6 ± 1.4 | 65.2 ± 1.4 | 66.4 ± 1.3 | 65.3 ± 1.4 | |
| Waist; cm | | | | | |
| GH | 111.8 ± 1.8 | 110.8 ± 1.8 | 107.6 ± 1.7 | 109.8 ± 1.9 | 0.002 |
| Placebo | 109.5 ± 2.5 | 109.4 ± 2.4 | 109.3 ± 2.3 | 111.0 ± 2.3 | |
| Sagittal diameter; cm | | | | | |
| GH | 26.1 ± 0.5 | 25.9 ± 0.5 | 25.2 ± 0.5 | 25.0 ± 0.6 | 0.03 |
| Placebo | 25.5 ± 0.7 | 25.3 ± 0.8 | 24.6 ± 0.9 | 25.5 ± 0.8 | |
| Visceral AT; cm² | | | | | |
| GH | 126 ± 15 | 121 ± 19 | 98 ± 14 | 99 ± 15 | 0.004 |
| Placebo | 163 ± 16 | 147 ± 13 | 142 ± 12 | 150 ± 13 | |

All values are expressed as the mean (SEM).
P-values denote the differences between the two groups by two-way ANOVA for repeated measurements.

TABLE 3

Measurements of glycosylated hemoglobin (HbA1c), C-peptide, total cholesterol, triglycerides, lipoprotein lipase (LPL) activity expressed as mU per gram of adipose tissue (AT), plasma fibrinogen and plasminogen activator inhibitor (PAI)-1 in 30 men, during 9 months of rhGH or placebo treatment.

| Variable | Baseline | 6 weeks | 6 months | 9 months | P# |
|---|---|---|---|---|---|
| HbA1c; % | | | | | |
| GH | 5.2 ± 0.1 | 5.2 ± 0.1 | 5.4 ± 0.1 | 5.3 ± 0.1 | 0.8 |
| Placebo | 4.9 ± 0.1 | 4.9 ± 0.1 | 5.0 ± 0.1 | 5.1 ± 0.2 | |
| C-peptide; ng/L | | | | | |
| GH | 1.11 ± 0.10 | 1.60 ± 0.13 | 1.30 ± 0.17 | 1.18 ± 0.07 | 0.02 |
| Placebo | 1.28 ± 0.27 | 1.30 ± 0.27 | 1.28 ± 0.32 | 1.42 ± 0.30 | |
| Total cholesterol; mmol/L | | | | | |
| GH | 6.1 ± 0.2 | 5.7 ± 0.2 | 6.1 ± 0.2 | 5.4 ± 0.3 | 0.006 |
| Placebo | 5.4 ± 0.3 | 5.6 ± 0.2 | 6.1 ± 0.3 | 5.5 ± 0.2 | |
| Triglycerides; mmol/L | | | | | |
| GH | 2.09 ± 0.29 | 2.60 ± 0.42 | 2.31 ± 0.23 | 1.78 ± 0.23 | 0.02 |
| Placebo | 1.65 ± 0.13 | 1.80 ± 0.20 | 1.85 ± 0.22 | 2.05 ± 0.26 | |
| LPL activity; mU/g AT | | | | | |
| GH | 287 ± 26 | 205 ± 15 | ND | 371 ± 65 | 0.2 |
| Placebo | 224 ± 31 | 228 ± 29 | ND | 263 ± 25 | |
| Fibrinogen; g/L | | | | | |
| GH | 31.3 ± 0.13 | 3.44 ± 0.10 | 3.49 ± 0.13 | 3.24 ± 0.19 | 0.04 |
| Placebo | 3.03 ± 0.11 | 2.73 ± 0.09 | 3.39 ± 0.28 | 2.84 ± 0.10 | |
| PAI-1 activity; U/mL | | | | | |
| GH | 31.3 ± 6.4 | 23.2 ± 2.6 | 18.3 ± 3.1 | 22.9 ± 3.5 | 0.4 |
| Placebo | 17.0 ± 3.8 | 22.9 ± 4.2 | 19.9 ± 4.5 | 27.1 ± 6.3 | |

All values are expressed as the mean (SEM).
P-values denote the differences between the two groups by two-way ANOVA for repeated measurements.

TABLE 4

Measurements of serum IGF-I, IGFBP-3, free fatty acids, (FFA), testosterone, and steroid hormone binding globulin (SHBG) in 30 men, during 9 months of GH/placebo treatment.

| Variable | Baseline | 6 weeks | 6 months | 9 months | P# |
|---|---|---|---|---|---|
| IGF-I; μg/L | | | | | |
| GH | 134 ± 8 | 338 ± 16 | 320 ± 23 | 268 ± 23 | <0.001 |
| Placebo | 120 ± 11 | 121 ± 11 | 129 ± 12 | 119 ± 12 | |
| IGF-I SD score* | | | | | |
| GH | −0.82 ± 0.17 | 3.30 ± 0.35 | 2.91 ± 0.49 | 1.89 ± 0.48 | <0.001 |
| Placebo | −1.07 ± 0.23 | −1.04 ± 0.23 | −0.87 ± 0.24 | −1.08 ± 0.25 | |
| IGFBP-3; mg/L | | | | | |
| GH | 2.36 ± 0.13 | 3.20 ± 0.10 | 3.19 ± 0.13 | 2.71 ± 0.14 | 0.001 |
| Placebo | 2.10 ± 0.16 | 2.21 ± 0.17 | 2.45 ± 0.21 | 2.18 ± 0.19 | |
| FFA; μmol/L | | | | | |
| GH | 0.77 ± 0.07 | 0.99 ± 0.11 | 0.78 ± 0.11 | 0.75 ± 0.07 | 0.5 |
| Placebo | 0.73 ± 0.05 | 0.73 ± 0.05 | 0.59 ± 0.06 | 0.67 ± 0.05 | |
| Testosterone; nmol/L | | | | | |
| GH | 14.6 ± 1.2 | 12.9 ± 1.0 | 13.9 ± 1.3 | 12.4 ± 1.1 | 0.12 |
| Placebo | 14.6 ± 1.0 | 15.4 ± 1.2 | 17.6 ± 2.1 | 14.6 ± 1.3 | |
| SHBG; nmol/L | | | | | |
| GH | 26.4 ± 3.4 | 25.5 ± 3.5 | 25.9 ± 3.1 | 23.4 ± 2.8 | 0.8 |
| Placebo | 28.1 ± 2.9 | 29.1 ± 3.1 | 29.2 ± 3.2 | 25.5 ± 2.7 | |

All values are expressed as the mean (SEM).
P-values denote the differences between the two groups by two-way ANOVA for repeated measurements.
*The standard deviation score for serum IGF-I is calculated from predicted IGF-I values adjusted for age and sex obtained from the normal population[18].

References

1. Björntorp P. Visceral obesity: A "Civilization syndrome". Obes Res 1993;1; 206–222.
2. Reaven G H. Role of insulin resistance in human disease. Diabetes 1988;37:1595–1607.
3. Bengtsson B-Å. The consequences of growth hormone deficiency in adults. Acta Endocrinol 1993;128 (Suppl 2):2–5.
4. Reaven G M. Pathophysiology of insulin resistance in human disease. Physiol Rev 1995;75486–473.

5. Salomon F, Cuneo R C, Hesp R, Sönksen P H. The effects of treatment with recombinant human growth hormone on body composition and metabolism in adults with growth hormone deficiency. N Engl J Med 1989;321:1797–1803.
6. Johansson J-O, Fowelin J, Landin K, Lager I, Bengtsson B-Å. Growth hormone-deficient adults are insulin-resistant. Metabolism 1995;44:1126–9.
7. Rosén T, Edén S, Larsson G, Wilhelmsen L, Bengtsson B-Å. Cardiovascular risk factors in adult patients with growth hormone deficiency. Acta Endocrinol 1993;129:195–200.
8. Johansson J-O, Landin K, Tengborn L, Rosén T, Bengtsson B-Å. High fibrinogen and plasminogen activator inhibitor activity in growth hormone deficient adults. Arterioscler Thromb 1994;14:434–7.
9. Markussis V, Beshyam S A, Fisher C, Sharp P, Nicolaides A N, Johnston D G. Detection of premature atherosclerosis by high-resolution ultrasonography in symptom-free hypopituitary adults. Lancet 1992;34:1188–92.
10. Marin P, Björntorp P. Endocrine-metabolic pattern and adipose tissue distribution. Horm Res 1993;39(suppl 3):81–85.
11. Rosén T, Bengtsson B-Å. Premature mortality due to cardiovascular diseases in hypopituitarism. Lancet 1990;336:285–88.
12. Marin P, Darin N, Amemiya T, Andersson B, Jern S, Björntorp P. Cortisol secretion in relation to body fat distribution in obese premenopausal women. Metabolism 1992;41:882–886.
13. Marin P, Kvist H, Lindstedt G, Sjöström L, Bjbrrtorp P. Low concentrations of insulin-like growth factor-I in abdominal obesity. Int J Obesity 1993;17:83–89.
14. Mirin P, Holmäng S, Gustafsson C, et al. Androgen treatment of abdominally obese men. Obes Res 1993;1:245–251.
15. Veldhuis J D, Liem A Y, South S, et al. Differential impact of age, sex steroid hormones, and obesity on basal versus pulsatile growth hormone secretion in men as assessed in an ultrasensitive chemiluminescence assay. J Clin Endocrinol Metab 1995;80:3209–22.
16. Hartman M L, Clayton P E, Johnson M L, et al. A low dose euglycemic infusion of recombinant human insilin-like growth factor I rapitly suppresses fasting-enhanced pulsatile growth hormone secretion in humans. J Clin Invest 1993;91:2453–2462.
17. De Boer H, Blok G-J, Van der Veen E A. Clinical aspects of growth hormone deficiency in adults. Endocr Rev 1995;16:63–86.
18. Landin-Wilhelmsen K, Wilhelmsen L, Lappas G, et al. Serum insulin-like growth factor I in a random population sample of men and women:relationship to age, sex, smoking habits, coffee consumption and physical activity, blood pressure and concentrations of plasma lipids, fibrinogen, parathyroid hormone and osteocalcin. Clin Endocrinol 1994;41:351–7.
19. Kvist H, Chowdhury B, Sjöström L, Tylén U, Cederblad Å. Adipose tissue volume determination in males by computed tomography and $^{40}K$. Int J Obesity 1988;12:249–266.
20. Chowdhury B, Sjöström L, Alpsten M, Konstanty J, Kvist H, Löfgren R. A multicompartment body composition technique based on computed tomography. Int J Obesity 1994;18:219–234.
21. Bengtsson-Olivecrona G, Olivecrona T. Lipoprotein analysis-a practical approach. Oxford: Oxford University Press, 1992. (Converse C A, Skinner E R, eds. Practical Approach Series;
22. Dole V P, Meinertz H. Microdetermination of long-chain fatty acids in plasma and tissues. J Biol Chem 1960;235:2595–2599.
23. Friberger P, Knös M, Gustavsson S, Aurell L, Claeson G. Methods for determination of plasmin, antiplasmin and plasminogen by means of substrate S-2251. Heamostasis 1978;7:138–145.
24. Larsson B, Seidell J, Svärdsudd K, et al. Obesity, adipose tissue distribution and health in men. The study of men born in 1913. Apetite 1989;13:37–44.
25. Marcus R, Butterfield G, Holloway L, et al. Effects of short-term administration of recombinant human growth hormone to elderly people. J Clin Endocrinol Metab 1990;70:519–27.
26. Rudman D, Feller A G, Nagraj H S, et al. Effects of human growth hormone in men over 60 years old. N Engl J Med 1990;323:1–6.
27. Bengtsori B-Å, Edén S, Lönn L, et al. Treatment of adults with growth hormone (GH) deficiency with recombinant human GH. Clin Endocrinol Metab 1993;76:309–317.
28. Rosenbaum M, Gertner J M, Leibel R. Effects of systemic growth hormone (GH) administration on regional adipose tissue distribution and metabolism in GH-deficient children. J Clin Endocrinol Metab 1989;69:1274–81.
29. Bolli G B, Gerich J E. The "dawn phenomenon"—A common occurrence in both non-insulin-dependent and insulin-dependent diabetes mellitus. N Engl J Med 1984;310:746–750.
30. Fowelin J, Attvall S, von Schenk H, Smith U, Lager I. Combined effect of growth hormone and cortisol on late posthypoglycaemic insulin resistance in humans. Diabetes 1989;38:1357–1364.
31. Fowelin J. Attvall S, Lager I, Bengtsson B-Å. Effects of treatment with recombinant human growth hormone on insulin sensitivity and glucose metabolism in adults with growth hormone deficiency. Metabolism 1993;42:1443–47.
32. DeFronzo R A, Gunnarsson R, Björkman O, Olsson M, Wahren J. Effects of insulin on peripheral and splanchnic glucose metabolism in non-insulin dependent diabetes mellitus. J Clin Invest 1985;76:149–155.
33. Lund S, Flyvbjerg A, Holman GD, Larsen FS, Pedersen O, Schmitz O. Comparative effects of IGF-I and insulin on the glucose transporter system in rat muscle. Am J Physiol 1994;267:E461–E466.
34. Ayling C M, Moreland B H, Zanelli J M, Schulster D. Human growth hormone treatment of hypophysectomized rats increases the proportion of type-1 fibres in skeletal muscle. J Endocinol 1989;123:429–435.
35. Rudling M, Norstedt G, Olivecrona H, Reihnér E, Gustafsson J-Å, Angelin B. Importance of growth hormone for the induction of hepatic low density lipoprotein receptors. Proc Natl Acad Sci USA 1992;89:6983–7.
36. Angelin B, Rudling M. Growth hormone and hepatic lipoprotein metabolism. Curr Opin Lipidol 1994;5:160–5.
37. Elam M B, Wilcox H G, Salomon S S, Heimberg M. In vivo growth hormone treatment stimulates secretion of very low density lipoproteins by the perfused rat liver. Endocrinology 1992;131:2717–22.
38. Richelsen B, Pedersen SB, BÒrglum J D, MÒller-Pedersen T, JÒrgensen J, JÒrgensen J O. Growth hormone treatment of obese women for 5 wk; effect on body composition and adipose tissue LPL activity. Am J Physiol 1994;266:E211–E216.
39. Caidahl K, Edén S, Bengtsson B-Å. Cardiovascular and renal effects of growth hormone. Clin Endocinol 1994;40:393–400.
40. Reaven G M, Lithell H. Landsberg L. Hypertension and associated metabolic abnormalities-the role of insulin resistance and the sympathoadrenal system. N Engl J Med 1996;334:374–381.
41. Copeland K C, Nair K S. Recombinant human insulin-like growth factor-I increases forearm blood flow. J Clin Endocrinol Metab 1994;79:230–2
42. Vague P, Juhan-Vague I, Aillaud M F, et al. Correlation between blood fibrinolytic activity, plasminogen activator inhibitor level, plasma insulin level, and relative body weight in normal and obese subjects. Metabolism 1986;35:250–253.
43. Landin K, Stigendal L, Eriksson E, et al. Abdominal obesity is associated with impaired fibrinolytic activity and elevated plasminogen activator inhibitor-1. Metabolism 1990;39:1044–1048.
44. Hamsten A, de Faire U, Walldius G, et al. Plasminogen activator inhibitor in plasma: risk factor for recurrent myocardial infarction. Lancet 1987;2:3–9.
45. Wilhelmsen L, Svärdsudd K, Korsan-Bengtsen K, Larsson B, Welin L, Tibblin G. Fibrinogen as a risk factor for stroke and myocardial infarction. N Engl J Med 1984;311:501–505.
46. Marin P, Holmäng S, Jönsson L, et al. The effects of testosterone treatment on body composition and metabolism in middle-aged obese men. Int J Obesity 1992;16:991–997.
47. Liu L, Merriam G R, Sherins R J. Chronic sex steroid exposure increases mean plasma growth hormone concentration and pulse amplitude in men with isolated hypogonadotropic hypogonadisum. J Clin Endocrnol Metab 1987;64:651–6.
48. Yang S, Xu X, Bjömtorp P, Edén S. Additative effects of growth hormone and testosterone on lipolysis in adipocytes of hypophysectomized rats. J Endocrinol 1995;147:147–152.

What is claimed is:

1. A method for treating a patient having Metabolic Syndrome comprising Primary Insulin Resistance and abdominal/visceral obesity to decrease insulin resistance, wherein said method comprises administering to said patient human growth hormone or a functional analog thereof in an amount effective for decreasing insulin resistance of said patient.

2. The method according to claim 1, wherein the treatment increases insulin sensitivity of the patient.

3. The method of according to claim 1 wherein the human growth hormone comprises recombinant human growth hormone or a functional analog thereof.

4. The method according to claim 3, wherein said method comprises administering recombinant human growth hormone at about 9.5 μg/kg daily.

* * * * *